United States Patent
Palepu et al.

(10) Patent No.: US 11,497,789 B2
(45) Date of Patent: *Nov. 15, 2022

(54) FORMULATIONS OF VANCOMYCIN

(71) Applicant: SciDose Pharma LLC, Amherst, MA (US)

(72) Inventors: Nagesh R. Palepu, Southampton, PA (US); Philip Christopher Buxton, Uxbridge (GB)

(73) Assignee: SCIDOSE PHARMA, LLC, Amherst, MA (US)

( * ) Notice: Subject to any disclaimer, the term of this patent is extended or adjusted under 35 U.S.C. 154(b) by 17 days.

This patent is subject to a terminal disclaimer.

(21) Appl. No.: 17/118,936

(22) Filed: Dec. 11, 2020

(65) Prior Publication Data

US 2021/0236592 A1    Aug. 5, 2021

Related U.S. Application Data

(63) Continuation of application No. 16/512,654, filed on Jul. 16, 2019, now Pat. No. 10,864,250, which is a continuation of application No. 15/405,884, filed on Jan. 13, 2017, now Pat. No. 10,376,559.

(60) Provisional application No. 62/279,210, filed on Jan. 15, 2016.

(51) Int. Cl.

| | | |
|---|---|---|
| *A61K 38/14* | (2006.01) | |
| *A61K 47/10* | (2017.01) | |
| *A61K 47/12* | (2006.01) | |
| *A61K 9/00* | (2006.01) | |
| *C07K 9/00* | (2006.01) | |
| *A61K 31/7042* | (2006.01) | |
| *A61K 9/08* | (2006.01) | |
| *A61K 47/02* | (2006.01) | |

(52) U.S. Cl.
CPC ............ *A61K 38/14* (2013.01); *A61K 9/0019* (2013.01); *A61K 9/08* (2013.01); *A61K 31/7042* (2013.01); *A61K 47/02* (2013.01); *A61K 47/10* (2013.01); *A61K 47/12* (2013.01); *C07K 9/00* (2013.01)

(58) Field of Classification Search
CPC ........ A61K 38/14; A61K 47/02; A61K 47/10; A61K 9/0019; A61K 9/08
See application file for complete search history.

(56) References Cited

U.S. PATENT DOCUMENTS

| | | |
|---|---|---|
| 4,885,275 A | 12/1989 | Robinson |
| 6,383,471 B1 | 5/2002 | Chen et al. |
| 7,364,874 B2 | 4/2008 | Totsuka et al. |
| 9,616,098 B2 | 4/2017 | Palepu |
| 10,376,559 B2 | 8/2019 | Palepu et al. |
| 10,864,250 B2 * | 12/2020 | Palepu .................. A61K 47/12 |
| 2003/0229047 A1 | 12/2003 | Joshi-Hangal et al. |
| 2016/0101147 A1 | 4/2016 | Palepu |
| 2017/0079910 A1 | 3/2017 | Muni et al. |
| 2017/0304396 A1 | 10/2017 | Chen |

FOREIGN PATENT DOCUMENTS

| | | |
|---|---|---|
| JP | 2008201778 A | 9/2008 |
| WO | 2012054447 A2 | 4/2012 |
| WO | 2014194296 A1 | 12/2014 |

OTHER PUBLICATIONS

International Search Report based on International Application No. PCT/US2014/040396 dated Oct. 15, 2014. (9 pages).
Vancomycin Drug Label (online) retrieved on Aug. 4, 2016 from: https://dailymed.nlm.nih.gov/dailymed/archives/fdaDrugInfo/cfm?archiveid=1651; 2006; 12 pages).
International Search Report based on International Application No. PCT/US2017/013389 dated Mar. 23, 2017. (5 pages).

* cited by examiner

*Primary Examiner* — James D. Anderson
(74) *Attorney, Agent, or Firm* — Lucas & Mercanti, LLP

(57) ABSTRACT

Liquid vancomycin containing compositions having extended shelf life are disclosed. The compositions contain vancomycin or a pharmaceutically acceptable salt thereof, a polyol such as glycerol, and lactic acid or a lactate. The compositions are ready to use and easily transferred into larger parenteral solutions prior to administration to patients in need thereof.

18 Claims, No Drawings

FORMULATIONS OF VANCOMYCIN

CROSS-REFERENCE TO RELATED APPLICATIONS

This application is a continuation of U.S. patent application Ser. No. 16/512,654, filed Jul. 16, 2019, which is a continuation of U.S. patent application Ser. No. 15/405,884, filed Jan. 13, 2017, now U.S. Pat. No. 10,376,559, which in turn claims the benefit of priority from U.S. Provisional Application Ser. No. 62/279,210, filed Jan. 15, 2016, the contents of each of which are incorporated herein by reference.

BACKGROUND OF THE INVENTION

Vancomycin is a glycopeptide antibiotic represented by the following structural formula (I):

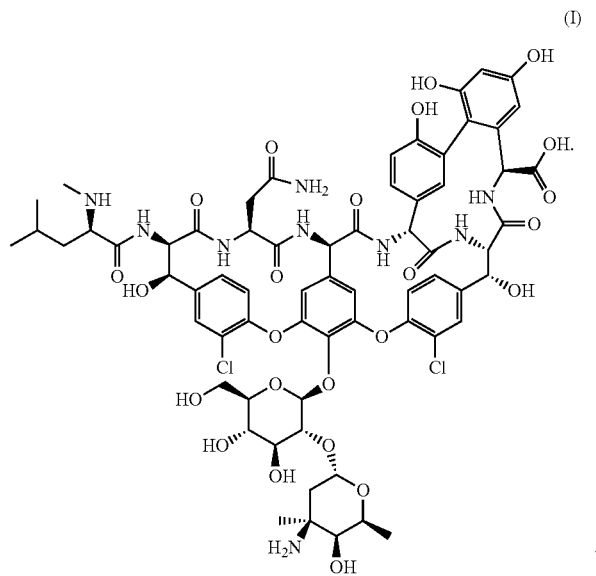

Vancomycin is used in the prophylaxis and treatment of infections caused by Gram-positive bacteria. Vancomycin is used in the treatment of methicillin-resistant *Staphylococcus aureus* (MRSA) and Methicillin-susceptible *Staphylococcus aureus* (MSSA), and to treat patients who are penicillin-resistant. Vancomycin HCl is commercially available inter cilia, as a frozen premixed formulation, which can be used for intravenous administration after thawing.

Vancomycin exhibits premature degradation after reconstitution of the lyophilized product. Vancomycin is stable in water for approximately 24 hours after reconstitution, and is therefore, not suitable for long-term storage in liquid form. There is a need for vancomycin formulations with increased stability. One solution to this to addresses this need is described in US Patent Application Publication No. 2016/0101147, the contents of which are incorporated herein by reference. This patent application discloses vancomycin formulations containing propylene glycol and/or polyethylene glycol. However, further innovations have been sought for certain patient populations, such as children or renally impaired patients where it may be advantageous to avoid propylene glycol and or PEG in intravenous products. Therefore, there is a continued need for new liquid vancomycin formulations with sufficient stability that can be delivered to patients.

It is generally known that vancomycin has a tendency to increase substantially in viscosity, for example to gel, at higher concentrations. It has also been disclosed that alcohols may be used for the reduction of this formation as noted in U.S. Pat. No. 4,885,275. However, glycerol (aka glycerine) did not prevent the formation of this gelation (see Table 1 therein, which noted that glycerine did not prevent the gelation of the vancomycin preparation). The '275 patent therefore teaches away from the use of glycerol in vancomycin compositions requiring lower viscosity.

SUMMARY OF THE INVENTION

The inventors have surprisingly found that glycerol can be used with compositions comprising higher concentrations of vancomycin. Surprisingly, it has also been found that in the present invention, glycerol can be used in high concentrations of vancomycin compositions, providing a formulation of sufficiently low viscosity to be able to be administered, e.g., as in an injection, as well as of sufficient stability to be commercially useful.

In some aspects of the invention, the liquid vancomycin-containing compositions include a) vancomycin or a pharmaceutically acceptable salt thereof; b) a polyol such as glycerol, c) one of lactic acid, a lactate salt or mixtures thereof; and optionally d) a pH adjustor, in an amount sufficient to maintain a pH of the vancomycin-containing composition at from about 4.5 to about 7.5, and in some aspects preferably at about 5.5 or 6.5.

The inventive compositions can be deemed to be concentrated vancomycin compositions which are "ready to use" in the sense that they are suitable for further dilution into a parenterally acceptable volumes of normal saline or the like and thereafter administered to a patient in need thereof.

In some aspects of the invention, the amount of vancomycin included in the compositions, as calculated on the basis of the free base, is from about 50 mg/mL to about 250 mg/mL, or from about 75 mg/mL to about 220 mg/mL. In some embodiments, the vancomycin concentration is preferably about 100 mg/mL. Upon dilution in the final parenteral volume, i.e. 200 ml, 500 ml, etc., IV bag, the amount of vancomycin as calculated on the basis of free base included in the compositions is from about 2.5 mg/mL to about 15 mg/mL.

In some aspects of the invention, the compositions include from about 15% (v/v) to about 50% glycerol. Some preferred aspects include about 20%, 25% or 30% glycerol, with amounts of about 25% being more preferred within these embodiments. Compositions according to the invention also include from about 0.125 M to about 1 M lactic acid or a lactate salt.

Still further aspects of the invention include methods of treatment using vancomycin-containing compositions and kits including the same.

It has been surprisingly found that the gelling phenomena commonly associated with vancomycin when present in liquids at concentrations of higher than about 100 mg/ml is substantially avoided with the liquid compositions described herein. Furthermore, the commonly observed increases in viscosity of vancomycin solutions expected in the presence of ever increasing concentrations of glycerin is also avoided as a result of the formulations described herein. Moreover, these formulations exhibit chemical and physical stability at commercially relevant temperatures, i.e. at room temperature or under refrigeration, and over commercially relevant time frames, i.e. about 1 year or longer.

One of the advantages of the liquid compositions prepared according to the current invention is that they have substantially improved long-term solution stability. In some aspects, the inventive vancomycin-containing compositions are substantially free of precipitation or crystal formation after at least about 12 months of storage at a temperature of from about 5° C. to about 25° C. In further aspects of the invention, the inventive vancomycin-containing compositions also exhibit levels of vancomycin B of at least about 88% of the original or starting content, as determined by high performance liquid chromatography ("HPLC") at a wavelength of 280 nm, after at least about 12 months of storage at a temperature of from about 5° C. to about 25° C.

As used herein, the vancomycin concentration is measured using the United States Pharmacopeia (USP) official monograph for vancomycin for injection described in USP 36, the contents of which are incorporated by reference herein.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

For purposes of the present invention, "substantially free of precipitation" shall be understood to include vancomycin-containing compositions in which precipitation is not visually observed after a period of at least about 12 months at a temperature of from about 5° C. to about 25° C. "Substantially free of total impurities" shall be understood to include vancomycin-containing compositions which exhibit levels of vancomycin B of at least about 88% of the original or starting content, as determined by HPLC at a wavelength of 280 nm, after at least about 12 months of storage at a temperature of from about 5° C. to about 25° C. Still further aspects include liquid vancomycin compositions which exhibit levels of vancomycin B of at least about, as determined by high performance liquid chromatography ("HPLC") at a wavelength of 280 nm, after at least about 18 months of storage at room temperature, i.e. about 18-20° C. The amount of impurities is further calculated as being based upon the original amount vancomycin B (or salt thereof) being present in the composition or formulation. In accordance with the USP official monograph for vancomycin, the concentration of vancomycin is determined by measuring the amount of vancomycin B by HPLC at a wavelength of 280 nm. For the detailed procedure used to calculate vancomycin B, refer to the USP monograph for vancomycin. In some examples, a normalized loss of vancomycin B may be calculated by dividing the concentration of vancomycin B at the testing point by the initial concentration of vancomycin B, and then multiplying by 100.

For purposes of the present invention, the polyol shall be understood to include pharmaceutically acceptable grades of glycerol (i.e. C3E1803), which is also called glycerine or glycerin. See also the current United States Pharmacopeia (USP) Glycerin monograph, the contents of which are incorporated herein by reference.

For purposes of the present invention, a "pharmaceutically acceptable fluid" is a fluid which is suitable for pharmaceutical use, for example but not limited to solvents, vehicles, large volume parenteral solutions (LVPs) such as water, water for injection (WFI), normal saline (i.e., 0.9% sodium chloride) or 5% dextrose in water ("D5W"), and/or additional diluents, or mixtures thereof, if desired, etc.

For purposes of the present invention, the term "about" shall be understood herein to mean less than or equal to a 5-10% deviation from the recited value, for example, a concentration of about 20% (v/v) means a concentration of 20%±5 or 10%.

The inventive compositions are substantially free of visible precipitation after at least about 12 months of storage at a temperature of from about 5° C. to about 25° C. Without being bound by theory, it is believed that the surprising long-term stability of solutions prepared according to the present invention arises at least in part from the interaction between lactic acid (or the lactate molecule used in certain embodiments), the glycerol, and the vancomycin.

In some aspects of the invention, the vancomycin is preferably present in the formulation as an HCl salt.

In some aspects of the invention, the vancomycin concentration calculated on the basis of the free base in the inventive compositions is from about 75 mg/mL to about 220 mg/mL, preferably about 100 mg/mL. In alternative aspects, the vancomycin concentration is about 200 mg/mL or otherwise in amounts which are sufficient for dilution into single or multiple administrations of dosages generally regarded as effective amounts.

The compositions of the present invention can be maintained at a pH of from about 4.5 to about 7.5. In some preferred embodiments, the composition is maintained at a pH of from about 5.5 to about 6.5. In at least one embodiment, the pH is about 5.5 while in another it is about 6.5.

In some embodiments of the invention, an optional pH adjustor is included in the vancomycin-containing compositions. The pH adjustor may take the form of one or more basic compounds or conjugates of acids present in an amount sufficient to adjust or maintain the pH of the composition to the range set forth above, i.e., from about 4.5 to about 7.5, or to specific points in between such as about 5.5 or about 6.5. One preferred base is sodium hydroxide. Alternative bases are those commonly used in the art, including TRIS or other amine buffers, sodium hydroxide and calcium hydroxide. In some aspects the concentration of the base to be used is about 1N or about 2N.

In some aspects of the invention, a lactate salt may be used in conjunction with or in place of lactic acid. In these embodiments, the optional pH adjustor may take the form of one or more acids or conjugate bases present in sufficient quantity to adjust the pH of the compositions to the ranges set forth above or to maintain the pH within these ranges, i.e., from about 4.5 to about 7.5. Alternative acids are those commonly used in the art, including but not limited to acetic acid, citric acid, hydrochloric acid, phosphoric acid and malic acid.

In some aspects of the invention where the concentration of vancomycin is in the range 50 to 250 mg/mL and the level of glycerol is between 15 and 50% v/v, the overall lactate concentration is set at an appropriate level to obtain a stabilizing effect. This level is preferably from about 0.25M to about 1.0M, more preferably from about 0.5M to about 0.75M. The level of lactate can derive from any enantiomeric form or mixture of enantiomeric forms of lactic acid or its salts such as D, L or preferably DL. The salt forms used can include but not be limited to sodium, calcium and magnesium. Before addition of the glycerol the pH is adjusted, e.g., within the range 4.5 to 6.5, by addition of appropriate bases or acids, such as sodium hydroxide or hydrochloric acid solutions. After addition of the glycerol the formula is made up to volume with WFI. A summary of the formulae is given below:

| Ingredient | Volume Concentration Range % v/v | Molar Concentration Range M | Weight Concentration Range Mg/mL |
|---|---|---|---|
| Vancomycin HCl | NA | 0.034 to 0.168 | 50 to 250 |
| Glycerol | 15 to 50 | 3.42 to 6.84 | 189 to 630 |
| Lactic Acid | NA | 0.25 to 1.00 | 22.5 to 90.0 |
| Sodium Lactate | NA | 0.25 to 1.00 | 28.3 to 113.0 |
| Calcium Lactate | NA | 0.125 to 0.5 | 27.3 to 109.0 |
| Magnesium Lactate | NA | 0.125 to 0.5 | 25.3 to 202.0 |
| pH | | 4.5 to 7.5 | |

Note:
Vancomycin concentrations expressed as pure free base, all other ingredients are anhydrous In an alternative aspect, the resulting final concentration of the lactic acid, lactate or mixtures thereof in the vancomycin-containing compositions of the present invention is preferably from about 0.25 mmole to about 0.94 mmole of lactic acid, lactate or mixtures thereof per mL of total vancomycin concentrate solution. This can be restated as about 22 to about 85 mg lactic acid per mL of total vancomycin concentrate solution. In some aspects, the final concentration of the lactic acid or lactate in the vancomycin-containing compositions of the present invention is about 0.75 mmole per mL of total vancomycin concentrate, alternatively stated as 0.75M, or about 67 mg lactic acid per mL of total vancomycin concentrate solution.

In some aspects of the invention, an antioxidant or free radical scavenging agent, e.g., methionine, is further included in the vancomycin-containing compositions. Other pharmaceutically-suitable antioxidants or free radical scavengers known in the art may be used, e.g., citric acid, ascorbic acid, sodium bisuifite, p-amino benzoic acid, glutathione, cysteine, methionine and N-acetyl cysteine.

Another embodiment of the invention includes methods of preparing the vancomycin-containing compositions described herein. The methods include combining bulk vancomycin in lyophilized or crystalline form with aqueous lactic acid or lactate solution, adjusting the pH to the desired range if needed, and thereafter combining it with the glycerol, so that the final concentration of the vancomycin is from about 75 mg/mL to about 220 mg/mL, preferably about 100 mg/mL. An optional pH adjustor (i.e., an acid or base or combination thereof) may also be included therein, in an amount sufficient to maintain the pH of the composition within the range disclosed above. Alternatively, one can also dissolve vancomycin a mixture of glycerol/lactic acid solution. The steps are preferably carried out under pharmaceutically acceptable conditions, e.g., for sterility assurance for eventual administration intravenously to a patient.

Alternatively the solutions can be made by simple addition, knowing the final amounts of each excipient desired in the formulation. For example, an appropriate percentage of the water can be taken, to which the desired amount of lactic acid is added and mixed. This mixture can be adjusted to pH. The desired amount of glycerol may be added and mixed into this solution. The vancomycin may then be added and dissolved into the mixture, the pH may then be adjusted, and the volume may be made up to the desired total with water. Then, the bulk solution may then be further processed as is appropriate for the intended use of the solution.

The compositions of the present invention may be packaged in any container suitable for the mode of use, such as in a sterile vial, infusion bag or container fit for the sterile or non-sterile storage of a pharmaceutical such as vancomycin. Suitable containers can be of a size sufficient to hold one or more doses of vancomycin. Within this aspect, from about 2 mL to about 200 mL of the inventive compositions are packaged as a single dose or a multi-dose product. Preferably, from about 5 mL to about 100 mL. Alternatively, sterile vial containers, for example, can contain about 2.5, 5, 7.5, 10, 20, 50 or 100 mL. In some aspects of the invention, the vancomycin concentration in the containers is from about 75 mg/mL to about 220 mg/mL. Preferably, the vancomycin concentration about 100 mg/mL and in alternative compositions it is up to about 200 mg/mL.

In other aspects, the containers include from 1 to about 25 doses, with doses generally being in the range of about 15 to 20 mg/kg IV every 8 to 12 hours for adults, for example. Preferably, the containers include from about 4 to about 20 doses, or from about 10 to about 20 doses. Stated alternatively, the sterile vials will contain from about 500 mg to up to about 10 grams of vancomycin. In some aspects, the vancomycin-containing compositions of the present invention will be packaged in a vial. Typical Type 1 glass vials are considered appropriate for injection or infusion vials. In other aspects, the compositions of the present invention will be packaged in an alternative package appropriate for the delivery of that composition.

A further aspect of the invention includes a kit containing the vancomycin-containing compositions described herein. As will be appreciated by those of ordinary skill, the kit will contain at least one pharmaceutically acceptable vial or container containing one or more doses of the vancomycin-containing compositions as well as other pharmaceutically necessary materials for storing and/or administering the drug, including instructions for storage and use, infusion bag or container with normal saline (i.e., 0.9% sodium chloride) or 5% dextrose in water ($D_5W$), and/or additional diluents, and mixtures thereof, if desired, etc.

In some embodiments, other excipients can also be added to adjust various properties of the formulation. For example, one or more antioxidants or free radical scavenging agents can be added to assist in improving the qualities of the product. An example antioxidant is methionine, which can be added in a range of from about 0.25 mg to about 10 mg/mL, or more preferably in some embodiments at a concentration of about 4 mg to about 6 mg/mL.

In some aspects of the invention, the inventive compositions are maintained during storage and/or prior to use at a temperature of from about 2° C. to about 10° C., i.e., under refrigerated conditions while in other aspects, the vancomycin compositions can be kept for extended periods at about room temperature.

Another embodiment of the invention includes methods of treating a vancomycin-sensitive disease in mammals, i.e., a bacterial infection. The methods include administering, to a mammal in need thereof, an effective amount of a vancomycin-containing composition described herein. Since the active ingredient portion of the inventive compositions is an FDA-approved drug, those of ordinary skill will recognize that the doses of vancomycin employed in this aspect of the invention will be the similar to those employed in any treatment regimens designed for vancomycin as marketed. The patient package inserts containing dosing information is incorporated herein by reference. The methods of treatment also include administering the inventive formulations for any purpose or physical condition for which vancomycin has been indicated as being useful. The daily intravenous dose is from about 1 g to about 2 g, administered as about 250 mg to about 500 mg every 3 to 6 hours or as about 1 g every 12 hours. Alternative dosing is from about 15 to 20 mg/kg IV every 8 to 12 hours. Alternative dosing in other modes of delivery is within the level of skill for the artisan administering the drug.

EXAMPLES

The following examples serve to provide further appreciation of the invention but are not meant in any way to restrict the effective scope of the invention.

Examples 1-3

100 mg/mL Vancomycin

Example 1

(75% (v/v) 1M Lactic Acid Solution and 25% (v/v) Glycerol)

A 1M lactic acid solution was prepared by dissolving 102.36 g of an 88% lactic acid solution in 1000 mL water for injection. The pH was then adjusted to 5.5 with a 2N sodium hydroxide solution. A 75:25 lactic acid:glycerol solution was prepared by combining 75 mL of this lactic acid solution with 25 mL of glycerol, and making up the volume to 100 mL with water for injection. 10 g of vancomycin HCl was then added to 75 ml of the 75:25 lactic acid:glycerol solution and the volume was made up to 100 mL with the 75:25 lactic acid:glycerol solution to yield a vancomycin concentration of 100 mg/mL. The sample was mixed well. 2N sodium hydroxide solution was added to the sample to bring the pH to 5.5.

Example 2

(80% (v/v) 1M Lactic Acid Solution and 20% (v/v) Glycerol)

An 80:20 lactic acid:glycerol solution was prepared by adding 20 mL of glycerol to 80 mL of the 1 M lactic acid solution prepared as described in Example 1, and the volume was made up to 100 mL with water for injection. 10 g of vancomycin HCl was then added to 75 mL of the 80:20 lactic acid:glycerol solution and the volume was made up to 100 mL with the 80:20 lactic acid: glycerol solution to yield a vancomycin concentration of 100 mg/mL. The sample was mixed well. 2N sodium hydroxide solution was added to the sample to bring the pH to 5.5.

Example 3

(85% (v/v) 1M lactic Acid Solution and 15% (v/v) Glycerol)

An 85:15 lactic acid:glycerol solution was prepared by adding 15 mL of glycerol to 85 mL of the 1M lactic acid solution prepared as described in Example 1, and the volume was made up to 100 mL with water for injection. 10 g of vancomycin HCl was then added to 85mL of the 85:15 lactic acid:glycerol solution and the volume was made up to 100 mL with the 85:15 lactic acid: glycerol solution to yield a vancomycin concentration of 100 mg/mL. The sample was mixed well. 2N sodium hydroxide solution was added to the sample to bring the pH to 5.5.

Control

A lactic acid solution was prepared by dissolving 10.24 g of an 88% lactic acid solution in 40 mL water for injection. The pH was then adjusted to 5.5 with a 2N sodium hydroxide solution. The volume was made up to 100 mL with water for injection. 10 g of vancomycin HCl was then added to the lactic acid solution to yield a vancomycin concentration of 100 mg/mL. The sample was mixed well. 2N sodium hydroxide solution was added to the sample to bring the pH to 5.5.

Each of the above compositions had samples aliquoted into vials, were sealed, were stored at 25° C. and were analyzed for visibly observable precipitation as reported in Table 1 below.

TABLE 1

Physical Stability of Vancomycin Solutions (100 mg/mL) at Various Levels of Glycerol, using Lactic Acid at 67.5 mg/mL adjusted to pH 5.5

| Example | Glycerol Concentration, % v/v (mg/mL) | Time to precipitation at 25° C. |
|---|---|---|
| 1 | 25% (315) | no precipitation for at least ~6 months |
| 2 | 20% (252) | no precipitation for at least ~6 months |
| 3 | 19.8% (250) | no precipitation for at least ~6 months |
| 4 | 17.8% (225) | no precipitation for at least ~6 months |
| 5 | 15.8% (200) | no precipitation for at least ~6 months |
| 6 | 15% (189) | N/A (Not followed at 25° C.) |
| 7 | 10% (126) | precipitation within days of preparation. |
| CONTROL | 0% (0) | precipitation within days of preparation. |

N/A - Not available

As shown in Table 1, the samples from Examples 1-6 including the combinations of lactic acid solution and glycerol demonstrate excellent stability. In contrast, the 10% v/v glycerol/lactic acid solution sample corresponding to Example 7 and the Control did not demonstrate physical stability. These samples exhibited precipitation shortly after preparation.

The chemical stability of these formulations further presented in the table below. In general, in pharmaceutical operations, stability at 3 mo at 40 C is representative of at least 12 month stability at 25° C.

TABLE 2

Chemical Stability of Vancomycin Solutions (100 mg/mL) at Various Levels of Glycerol, using Lactic Acid at 67.5 mg/mL adjusted to pH 5.5

| Glycerol, % v/v (mg/mL) | Temp/ period | % of VCM B | % Initial | Deg 1 | Deg 2 | Σ UK | % Total |
|---|---|---|---|---|---|---|---|
| 15% | Initial | 96.6 | 100 | 0.41 | 1.68 | 1.26 | 3.35 |
| (189) (Ex. 6) | 40° C. - 2 M | 90.7 | 93.9 | 1.85 | 4.85 | 2.65 | 9.35 |
| 15.8% | Initial | 96.7 | 100 | 0.37 | 1.16 | 1.20 | 2.73 |
| (200) (Ex. 5) | 40° C. - 3 M | 90.6 | 93.6 | 1.50 | 1.63 | 6.29 | 9.42 |
| | 25° C. - 6 M | 94.5 | 97.6 | 0.92 | 1.21 | 3.42 | 5.55 |
| 17.8% | Initial | 96.7 | 100 | 0.48 | 1.34 | 1.39 | 3.21 |
| (225) (Ex. 4) | 40° C. - 3 M | 90.1 | 93.1 | 1.50 | 1.62 | 6.83 | 9.95 |
| | 25° C. - 6 M | 94.6 | 97.7 | 0.91 | 1.25 | 3.20 | 5.36 |
| 19.8% | Initial | 96.8 | 100 | 0.45 | 1.30 | 1.48 | 3.23 |
| (250) Ex. 3) | 40° C. - 3 M | 90.0 | 93.0 | 1.55 | 1.62 | 6.88 | 10.05 |
| | 25° C. - 6 M | 94.5 | 97.6 | 0.83 | 1.27 | 3.94 | 6.04 |
| 20% | Initial | 96.2 | 100 | 0.28 | 1.66 | 1.82 | 3.76 |
| (252) (Ex. 2) | 40° C. - 3 M | 89.4 | 92.9 | 1.81 | 4.33 | 4.46 | 10.6 |
| | 25° C. - 6 M | 93.6 | 97.3 | 0.72 | 1.51 | 4.71 | 6.40 |
| | 5° C. - 6 M | 95.6 | 99.4 | 0.96 | 0.96 | 3.23 | 4.36 |
| 25% | Initial | 96.2 | 100 | 0.28 | 1.66 | 1.82 | 3.76 |
| (315) (Ex 1.) | 40° C. - 3 M | 90.2 | 93.8 | 2.03 | 4.31 | 3.47 | 9.81 |
| | 25° C. - 6 M | 95.5 | 99.3 | 0.86 | 1.43 | 2.26 | 4.55 |
| | 5° C. - 6 M | 96.0 | 99.8 | 0.20 | 0.91 | 2.93 | 4.04 |

N.B.: VCM B = Vancomycin B

As can be seen from the above, all of the compositions containing 15% or greater glycerol demonstrated long term stability under accelerated conditions sufficient to meet the desired endpoints of time and levels of vancomycin B.

Examples 8-15

Further examples of the inventive formulations were also prepared following the procedures of Examples 2-6.

| Example | Vancomycin mg/mL | Lactic Acid mg/mL | Glycerol % (v/v) | pH |
|---|---|---|---|---|
| 8 | 100 | 67.56 | 25 | 4.5 |
| 9 | 100 | 67.56 | 25 | 5.5 |
| 10 | 100 | 67.56 | 25 | 6.5 |
| 11 | 100 | 45.04 | 25 | 5.5 |
| 12 | 100 | 90.08 | 25 | 5.5 |
| 13 | 100 | 67.56 | 20 | 5.5 |
| 14 | 100 | 67.56 | 30 | 5.5 |
| 15 | 200 | 67.56 | 25 | 5.5 |

Example 16

As demonstrated in the table below, this combination of ingredients maintains a low viscosity even in the presence of glycerol and higher concentrations of vancomycin.

| Formulation | Vancomycin Concentration, mg/mL | Viscosity, cPs, 25° C. |
|---|---|---|
| Glycerol: 315 mg/mL, | 0 | 2.85 |
| Lactic Acid: 67.5 mg/mL | 100 | 5.34 |
| Water for Injection: qs to 1 mL pH 5.5 | 200 | 10.31 |

We claim:

1. A liquid vancomycin-containing composition, comprising of from about 50 mg/mL to about 250 mg/mL of vancomycin or a pharmaceutically acceptable salt thereof, glycerol, a member of the group consisting of lactic acid, lactate or mixtures thereof, a base and a pharmaceutically acceptable fluid containing water, said vancomycin-containing composition being suitable for parenteral administration, wherein the amount of glycerol is from about 15 to about 30% (v/v).

2. The liquid vancomycin-containing composition of claim 1, wherein the concentration of the vancomycin or pharmaceutically acceptable salt thereof is about 100mg/mL.

3. The liquid vancomycin-containing composition of claim 1, wherein the amount of glycerol is about 25% (v/v).

4. The liquid vancomycin-containing composition of claim 1, wherein the base is selected from the group consisting of an amine buffer, sodium hydroxide, calcium hydroxide, and mixtures thereof.

5. The liquid vancomycin-containing composition of claim 4, wherein the base is sodium hydroxide.

6. The liquid vancomycin-containing composition of claim 1, wherein the amount of lactic acid in the composition is from about 0.25 M to about 1.0 M.

7. A liquid vancomycin-containing composition, consisting of about 75 mg/mL to about 220 mg/mL vancomycin or a pharmaceutically acceptable salt thereof; about 15% (v/v) to about 30% (v/v) glycerol, a stabilizing amount of a member of the group consisting of lactic acid, lactate or mixtures thereof, a base, water, and optionally an acid pH adjustor, wherein the liquid vancomycin containing composition is suitable for intravenous administration.

8. The liquid vancomycin-containing composition of claim 7, wherein the amount of glycerol is 25% (v/v).

9. A method of treating a bacterial infection in mammals, comprising administering an effective amount of the liquid vancomycin-containing composition of claim 1 to a mammal in need thereof.

10. A method of treating a bacterial infection in mammals, comprising administering an effective amount of the liquid vancomycin-containing composition of claim 7 to a mammal in need thereof.

11. A kit comprising at least one pharmaceutically acceptable vial or container containing one or more doses of a liquid vancomycin-containing composition according to claim 1, and optionally a) instructions for use thereof in mammals and/or b) an infusion bag or container containing a pharmaceutically acceptable diluent.

12. The liquid vancomycin-containing composition of claim 1, further comprising an acid pH adjustor.

13. The liquid vancomycin-containing composition of claim 12, wherein the acid pH adjustor is selected from the group consisting of acetic acid, citric acid, hydrochloric acid, phosphoric acid and malic acid.

14. The liquid vancomycin-containing composition of claim 13, wherein the acid pH adjustor is hydrochloric acid.

15. The liquid vancomycin-containing composition of claim 7, wherein the acid pH adjustor is selected from the group consisting of acetic acid, citric acid, hydrochloric acid, phosphoric acid and malic acid.

16. The liquid vancomycin-containing composition of claim 15, wherein the acid pH adjustor is hydrochloric acid.

17. The liquid vancomycin-containing composition of claim 1, wherein the pH of the liquid vancomycin-containing composition is from about 4.5 to about 6.5.

18. The liquid vancomycin-containing composition of claim 7, wherein the pH of the liquid vancomycin-containing composition is from about 4.5 to about 6.5.

\* \* \* \* \*